(12) United States Patent
Reich et al.

(10) Patent No.: US 9,586,091 B2
(45) Date of Patent: *Mar. 7, 2017

(54) REMOTE ADAPTIVE MOTOR RESISTANCE TRAINING EXERCISE APPARATUS AND METHOD OF USE THEREOF

(71) Applicants: Alton Reich, Huntsville, AL (US); James Shaw, Sterling, CT (US)

(72) Inventors: Alton Reich, Huntsville, AL (US); James Shaw, Sterling, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/005,928

(22) Filed: Jan. 25, 2016

(65) Prior Publication Data

US 2016/0136483 A1    May 19, 2016

Related U.S. Application Data

(63) Continuation of application No. 13/737,735, filed on Jan. 9, 2013, now Pat. No. 9,272,186, which is a continuation-in-part of application No. 12/545,324, filed on Aug. 21, 2009, now abandoned, and a continuation-in-part of application No. 13/010,909, filed on Jan. 21, 2011.

(60) Provisional application No. 61/091,240, filed on Aug. 22, 2008, provisional application No. 61/387,772, filed on Sep. 29, 2010, provisional application No.
(Continued)

(51) Int. Cl.
*A63B 24/00* (2006.01)
*A63B 21/005* (2006.01)

(52) U.S. Cl.
CPC ...... *A63B 24/0087* (2013.01); *A63B 21/0058* (2013.01); *A63B 24/0062* (2013.01); *A63B 24/0084* (2013.01); *A63B 2024/0093* (2013.01); *A63B 2220/40* (2013.01); *A63B 2220/51* (2013.01); *A63B 2230/045* (2013.01)

(58) Field of Classification Search
CPC . A63B 24/00; A63B 24/0087; A63B 24/0062; A63B 24/0084; A63B 21/0058; A63B 2024/0093; A63B 2220/40; A63B 2220/51; A63B 2230/045
See application file for complete search history.

(56) References Cited

U.S. PATENT DOCUMENTS

| 4,869,497 A * | 9/1989 | Stewart | A63B 21/00178 482/5 |
| 5,980,435 A * | 11/1999 | Joutras | A43B 1/0054 482/114 |

(Continued)

*Primary Examiner* — Glenn Richman
(74) *Attorney, Agent, or Firm* — Kevin Hazen

(57) ABSTRACT

The invention comprises a method and/or an apparatus using a computer configured exercise system equipped with an electric motor to provide physical resistance to user motion in conjunction with means for sharing exercise system related data and/or user performance data with a secondary user, such as a medical professional, a physical therapist, a trainer, a computer generated competitor, and/or a human competitor. For example, the exercise system is used with a remote trainer to enhance exercise performance, with a remote medical professional for rehabilitation, and/or with a competitor in a competition, such as in a power/weightlifting competition or in a video game. The exercise system is optionally configured with an intelligent software assistant and knowledge navigator functioning as a personal assistant application.

20 Claims, 6 Drawing Sheets

Related U.S. Application Data

61/588,327, filed on Jan. 19, 2012, provisional application No. 61/591,699, filed on Jan. 27, 2012, provisional application No. 61/591,712, filed on Jan. 27, 2012.

(56) References Cited

U.S. PATENT DOCUMENTS

| | | | |
|---|---|---|---|
| 6,786,847 B1 * | 9/2004 | Morgan | A63B 21/012 482/142 |
| 7,942,783 B2 * | 5/2011 | Ochi | A61H 1/0244 482/1 |
| 8,398,546 B2 * | 3/2013 | Pacione | A61B 5/411 128/920 |
| 2002/0061804 A1 * | 5/2002 | Hasegawa | A61H 1/0214 482/57 |
| 2011/0287896 A1 * | 11/2011 | Kim | A63B 21/065 482/8 |

* cited by examiner

REMOTE ADAPTIVE MOTOR RESISTANCE TRAINING EXERCISE APPARATUS AND METHOD OF USE THEREOF

CROSS-REFERENCES TO RELATED APPLICATIONS

This application is a continuation of U.S. patent application Ser. No. 13/737,735 filed Jan. 9, 2013, which:

is a continuation in part of U.S. patent application Ser. No. 12/545,324, filed Aug. 21, 2009, which under 35 U.S.C. 120 claims benefit of U.S. provisional patent application No. 61/091,240 filed Aug. 22, 2008;

is a continuation in part of U.S. patent application Ser. No. 13/010,909, filed Jan. 21, 2011, which under 35 U.S.C. 120 claims benefit of U.S. provisional patent application No. 61/387,772 filed Sep. 29, 2010;

claims benefit of U.S. provisional patent application No. 61/588,327 filed Jan. 19, 2012;

claims benefit of U.S. provisional patent application No. 61/591,699 filed Jan. 27, 2012; and claims benefit of U.S. provisional patent application No. 61/591,712 filed Jan. 27, 2012, all of which are incorporated herein in their entirety by this reference thereto.

STATEMENT REGARDING FEDERALLY SPONSORED RESEARCH OR DEVELOPMENT

The U.S. Government may have certain rights to this invention pursuant to NASA SBIR Contract number: NNX10CB13C dated Feb. 5, 2010.

BACKGROUND OF THE INVENTION

1. Field of the Invention

The present invention relates generally to a computer and motor assisted exercise equipment apparatus and method of use thereof.

2. Discussion of the Related Art

Patents related to computer controlled variable resistance exercise equipment are summarized herein.

Sensors and Resistive Force

J. Casler, "Electronically Controlled Force Application Mechanism for Exercise Machines", U.S. Pat. No. 5,015,926 (May 14, 1991) describes an exercise machine equipped with a constant speed electric drive mechanically coupled to a dynamic clutch, which is coupled to an electromagnetic coil or fluid clutch to control rotary force input. An electronic sensor connected to a computer senses the speed, motion, and torque force of the system's output shaft and a control unit directed by the computer controls the clutch.

G. Stewart, et. al., "Computer Controlled Exercise Machine", U.S. Pat. No. 4,869,497 (Sep. 26, 1989) describe a computer controlled exercise machine where the user selects an exercise mode and its profile by programming a computer. Signals are produced by the program to control a resistive force producing device. Sensors produce data signals corresponding to the actuating member of the system, velocity of movement, and angular position. The sampled data are used to control the amount of resistive force.

Pressure/Movement Sensors

M. Martikka, et. al., "Method and Device for Measuring Exercise Level During Exercise and for Measuring Fatigue", U.S. Pat. No. 7,764,990 B2 (Jul. 27, 2010) describe sensors for measuring electrical signals produced by muscles during exercise and use of the electrical signals to generate a fatigue estimate.

E. Farinelli, et. al., "Exercise Intra-Repetition Assessment System", U.S. Pat. No. 7,470,216 B2 (Dec. 30, 2008) describe an intra-repetition exercise system comparing actual performance to a pre-established goal with each repetition of the exercise, where displayed indicia includes travel distance and speed.

R. Havriluk, et. al., "Method and Apparatus for Measuring Pressure Exerted During Aquatic and Land-Based Therapy, Exercise and Athletic Performance", U.S. Pat. No. 5,258,927 (Nov. 2, 1993) describe a device for monitoring exercise pressure on systems using an enclosed compressible fluid chamber. Measurements are taken at pressure ports and are converted to a digital signal for computer evaluation of type and degree of exercise performed.

Hand Controls

S. Owens, "Exercise Apparatus Providing Resistance Variable During Operation", U.S. Pat. No. 4,934,692 (Jun. 19, 1990) describes an exercise device having a pedal and hand crank connected to a flywheel provided with a braking mechanism. To vary the amount of braking, switches located on the hand crank are used making removal of the hand from the crank unnecessary to operation of the switches.

Resistance/Varying Resistance Exercise

D. Munson, et. al., "Exercise Apparatus Based on a Variable Mode Hydraulic Cylinder and Method for Same", U.S. Pat. No. 7,762,934 B1 (Jul. 27, 2010) describe an exercise machine having a hydraulic cylinder sealed with spool valves adjustable to permit entrance and exit of water with forces corresponding to forces exerted on the cylinder.

C. Hulls, "Multiple Resistance Curves Used to Vary Resistance in Exercise Apparatus", U.S. Pat. No. 7,682,295 B2 (Mar. 23, 2010) describes an exercise machine having varying resistance based on placement of a cable pivot point within a channel, where placement of the pivot point within the channel alters the resistance pattern along the range of motion of an exercise.

D. Ashby, et. al., "System and Method for Selective Adjustment of Exercise Apparatus", U.S. Pat. No. 7,645,212 B2 (Jan. 12, 2010) describe an electronic interface allowing adjustment of speed and grade level via a computer based interface mounted on an exercise machine, such as on a treadmill.

M. Anjanappa, et. al., "Method of Using and Apparatus for Use with Exercise Machines to Achieve Programmable Variable Resistance", U.S. Pat. No. 5,583,403 (Dec. 10, 1996) describes an exercise machine having a constant torque, variable speed, reversible motor, and associated clutches. The motor and clutch are chosen in a predetermined combination through use of a computer controller.

J. Daniels, "Variable Resistance Exercise Device", U.S. Pat. No. 5,409,435 (Apr. 25, 1995) describes a programmable variable resistance exercise device providing a resisting force to a user supplied force. The user supplied force is resisted by varying the viscosity of a variable viscosity fluid that surrounds plates rotated by the user applied force. A gear and clutch system allow resistance to a pulling force.

M. Brown, et. al., "User Force Application Device for an Exercise, Physical Therapy, or Rehabilitation Apparatus", U.S. Pat. No. 5,362,298 (Nov. 8, 1994) describe an exercise apparatus having a cable connected to a resistive weight and a detachable handle connected to the cable via a tension transmitting device.

Physiological Response

M. Lee, et. al., "Exercise Treadmill with Variable Response to Foot Impact Induced Speed Variation", U.S. Pat. No. 5,476,430 (Dec. 19, 1995) describe an exercise treadmill having a plurality of rates of restoration of the tread belt speed upon occurrence of change in the load on the moving tread belt resulting from the user's foot plant, where the user can select a desired rate of response referred to as stiffness or softness.

Power Generation/Energy Consumption

J. Seliber, "Resistance and Power Monitoring Device and System for Exercise Equipment", U.S. Pat. No. 7,351,187 B2 (Apr. 1, 2008) describes an exercise bike including pedals, a belt, and a hydrodynamic brake. User applied force to the pedals is transferred to a flywheel and relative rotation speeds of impellers of the fluid brake are used to estimate generated wattage.

J. Seo, et. al., "Apparatus and Method for Measuring Quantity of Physical Exercise Using Acceleration Sensor", U.S. Pat. No. 7,334,472 B2 (Feb. 26, 2008) describe a method for measuring calorie consumption when using an exercise device based upon generating acceleration information from an acceleration sensor.

S. Shu, et. al., "Power Controlled Exercising Machine and Method for Controlling the Same", U.S. Pat. No. 6,511,402 B2 (Jan. 28, 2003) describe a self-contained exercise machine with a generator and an alternator used to recharge a battery with power supplied from a stepper interface used by a subject.

Statement of the Problem

While a wide variety of computer-controlled systems exist, they lack real resistance and communication capabilities with remotely located secondary users.

What is needed is an exercise system that shares data with a remote secondary user.

SUMMARY OF THE INVENTION

The invention comprises a computer assisted exercise equipment method and apparatus configurable for linkage with a secondary user.

DETAILED DESCRIPTION OF THE INVENTION

Figure 1:
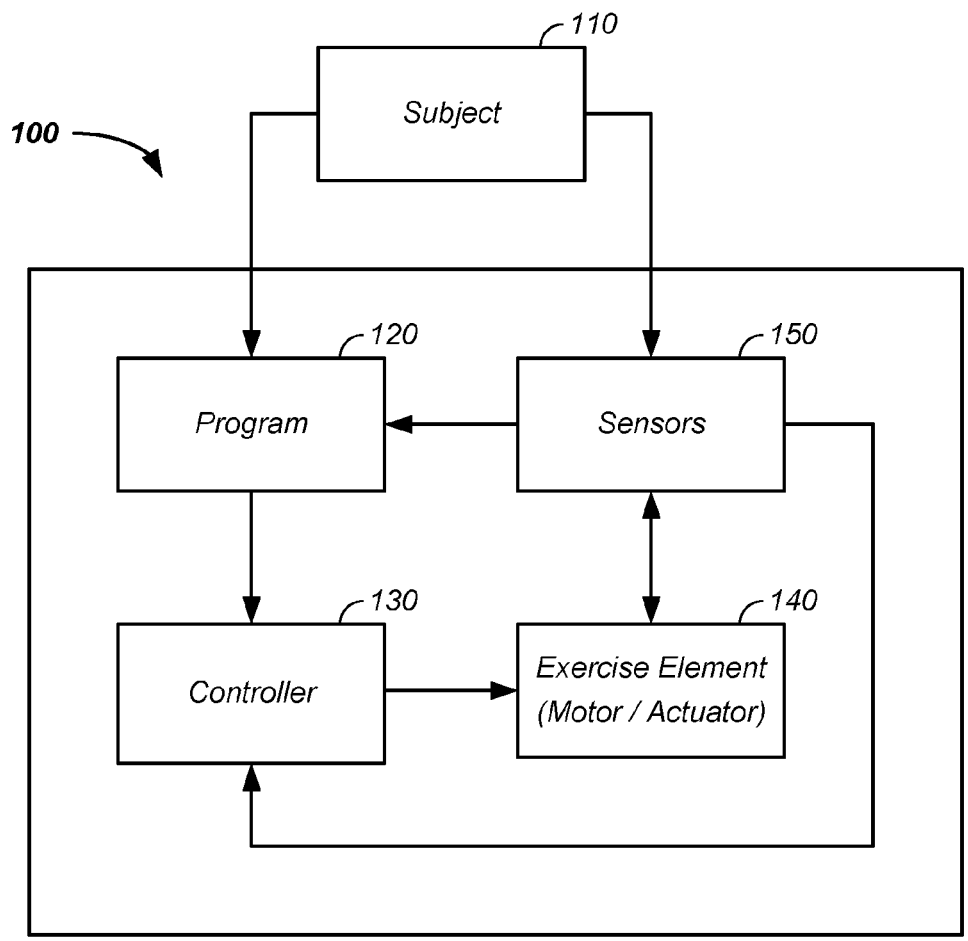
FIG. 1 provides a block diagram of an electric motor resistance based exercise system.

The invention comprises a method and/or an apparatus using a computer and electric motor equipped exercise apparatus additionally configured for remote communication with a secondary user.

In one embodiment, the system is a method and/or an apparatus using a computer configured exercise system equipped with an electric motor to provide physical resistance to user motion in conjunction with means for sharing exercise system related data and/or user performance data with a secondary user, such as a medical professional, a physical therapist, a trainer, a computer generated competitor, and/or a human competitor. For example, the exercise system is used with a remote trainer to enhance exercise performance, with a remote medical professional for rehabilitation, and/or with a competitor in a competition, such as in a power/weightlifting competition or in a video game. The exercise system is optionally configured with an intelligent software assistant and knowledge navigator functioning as a personal assistant application.

In another embodiment, an exercise system is used in conjunction with a gaming system, such as a video game system where the exercise system provides real physical resistance to a user interface. Results of user interaction with the user interface are integrated into a video game, such as running on a game console.

In yet another embodiment, an exercise system is described that includes: a moveable user interface element, an electric motor configured to supply a movement force to movement of the user interface element, and a controller electrically connected to the motor. Preferably, the movement force is configured to provide at least one of: (1) a resistive force against movement of the interface element by the user and (2) an assistive force aiding movement of the interface element by the user. The controller is preferably configured to control operation of the electric motor. Optionally, the controller is configured with at least one force profile. Herein a force profile is a set of forces or resistances supplied by the electric motor as a function of time and/or a set of forces or resistances as a function of relative movement position of a movable element of the exercise system and/or a set of forces or resistances calculated using an algorithm that takes as input any of the following:

the force applied to the interface element by the user;

the velocity of the interface element;

the acceleration of the interface element; and the power applied to the interface element by the user.

In still yet another embodiment, an exercise apparatus for operation by a user or a method of use thereof, includes a user interface having at least one of: (1) an element moveable along an about linear path and/or (2) a rotatable element. An electric motor is configured to supply an assistive and/or resistive force to movement of the user interface, such as via a cable or a linkage. Optionally, a controller is configured to control operation of the electric motor where the controller is configured with computer readable code controlling profile resistance as a function of time and/or distance within a portion of a repetition of movement of an element interfacing with a user of the exercise apparatus.

In yet still another embodiment, exercise equipment configured with a rotatable crank and means for varying resistance to rotation of the rotatable crank using an electric motor is described.

In still yet another embodiment, exercise equipment is configured with an electric motor resistance system. Resistance to movement supplied by the electric motor optionally varies dependent upon input from one or more subject sensors. Variation in resistive force optionally occurs:

within a single direction of a weight training repetition;

between directions of a weight training repetition; and/or between repetitions within a single set of repetitions.

Herein, a repetition is one complete movement of an exercise and repetitions refers to the number of times each exercise is completed in a row or in a set.

In yet still further another embodiment, a computer-controlled robotic resistance system or mechanical resistance training system is used for:
- entertainment;
- strength training;
- aerobic conditioning;
- low gravity training;
- physical therapy;
- rehabilitation; and/or
- medical diagnosis.

The resistance system comprises: a subject interface, software control, a controller, an electric motor, an electric servo assist/resist motor, a variable speed motor, an actuator, and/or a subject sensor. The resistance system is adaptable to multiple configurations to provide different types of training, as described infra.

The resistance system significantly advances neuromuscular function as it is adaptable to a level of resistance or applied force. For example, the system optionally uses:
- biomechanical feedback
- motorized strength training;
- motorized physical conditioning; and/or
- a computer programmed workout.

For example, a system is provided that overcomes the limitations of the existing robotic rehabilitation, weight training, and cardiovascular training systems by providing a training and/or rehabilitation system that adapts a resistance or force applied to a user interactive element in response to:
- the user's interaction with the training system;
- a physiological strength curve;
- sensor feedback;
- a computer game environment; and/or
- observations of the system.

For instance, the system optionally provides for an automatic reconfiguration and/or adaptive load adjustment based upon real time measurement of a user's interaction with the system or sensor based observation by the exercise system as it is operated by the subject 110.

Definitions

Herein, the human, person, and/or operator using the resistance system is referred to as a subject. The subject or user is any of: a trainer, a trainee, a video game player, a lifter, and/or a patient.

Herein, a computer refers to a system that transforms information in any way. The computer or electronic device, such as an embedded computer, a controller, and/or a programmable machine, is used in control of the exercise equipment.

Herein, an x-axis and a y-axis form a plane parallel to a support surface, such as a floor, and a z-axis runs normal to the x/y-plane, such as along an axis aligned with gravity. In embodiments used in low gravity space, the axes are relative to a support surface and/or to the subject 110.

Motor Assisted Resistance System

Referring now to FIG. 1, a block diagram of a motor equipped exercise system 100 is provided. As the exercise system 100 optionally provides resistance and/or assistance to a motion of user interface, such as a weightlifting bar or crank system, the motor equipped exercise system 100 is also referred to as a motor equipped resistance system, a resistance system, a motor equipped assistance system, and/or an assistance system. For clarity of presentation, examples provided herein refer to a resistance provided by a motor of the exercise system 100. However, the motor of the exercise system 100 is alternatively configured to provide assistance. Hence, examples referring to motor supplied resistance are non-limiting and in many cases the system is alternatively reconfigured to use motor supplied assistance in the range of motion of a particular exercise.

In one example, the user interface is directly contacted and moved by the user. In a second example, the user interface does not contact the user; however, the user interface is indirectly moved by the user.

Still referring to FIG. 1, the exercise system 100 includes one or more of: a computer configured with a program 120, a controller 130, an exercise element 140, and/or a sensor 150. The exercise system 100 is optionally configured for use and/or configuration by a subject 110 or a remote trainer/physical therapist.

Still referring to FIG. 1, the subject 110:
- enters a program 120 to the resistance system;
- alters the resistance of the exercise system 100 within a repetition;
- alters the resistance of the exercise system 100 between repetitions;
- is sensed by sensors 150 in the resistance system; and/or
- is recognized by the resistance system, such as through wireless means described infra.

The program 120 is optionally predetermined, has preset options, is configurable to a specific subject, changes resistance dynamically based on sensor input, and/or changes resistance based on subject input, described infra. The program 120 provides input to a controller 130 and/or a set of controllers, which controls one or more actuators and/or one or more motors of an exercise element 140 of the exercise system 100. Optional sensors provide feedback information about the subject 110 and/or the state of a current exercise movement, such as a position, velocity, and/or acceleration of a moveable element of the resistance system, a force applied to a portion of the exercise system 100, the subject's heart rate, and/or the subject's blood pressure. Signal from the sensors 150 are optionally fed in a feedback system or loop to the program 120 and/or directly to the controller 130. For example, the heart rate of the user is measured using a heart rate monitor and the physical resistance supplied by the electric motor is varied to maintain the heart rate in a target zone.

Optionally, active computer control is coupled with motorized resistance in the exercise system 100. The computer controlled motor allows for incorporation of progressive and reconfigurable procedures in strength training, physical conditioning, and/or cardiovascular exercise. For example, computer control of the motor additionally optionally provides resistance curves overcoming the traditional limits of gravity based freestyle weightlifting, described infra.

Linear Movement

Figure 2:
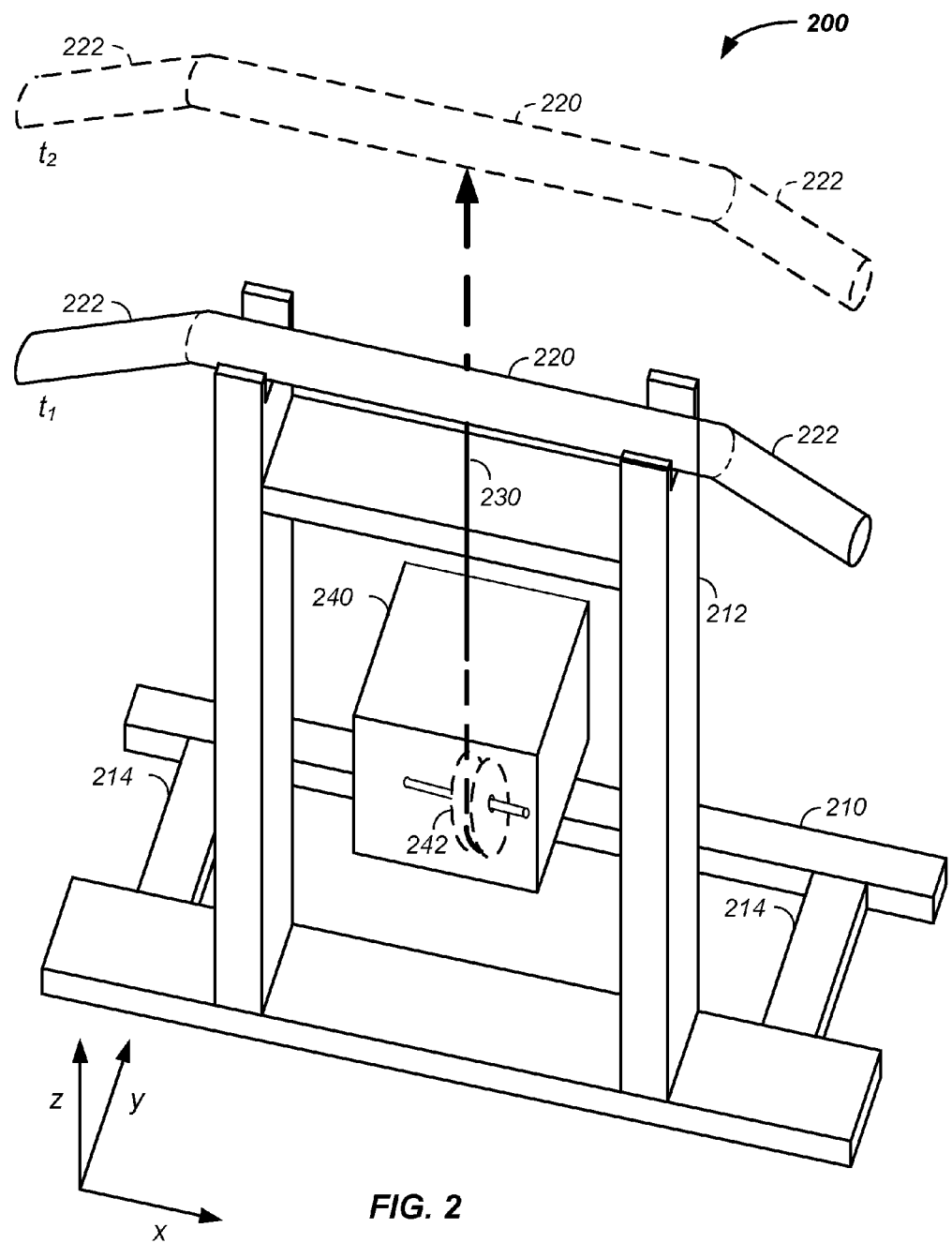
FIG. 2 illustrates hardware elements of an exemplary computer aided motorized resistance exercise system.

Referring now to FIG. 2, a non-limiting example of a linear movement system 200 is illustrated, which is a species of the exercise system 100. The linear movement system 200 is illustrative in nature and is used for facilitating disclosure of the system. Further, the species of the linear movement system 200 is to a specific form of the exercise system 100. However, the illustrated linear movement system 200 is only one of many possible forms of the exercise system 100 and is not limiting in scope. Herein the linear movement system refers to a linear, about linear, or non-rotational movement of the user interface exercise equipment, such as a weightlifting bar, or to movement of a resistance cable. Additionally, the linear movement system refers to a substantially linear, but curved movement of the user interface resultant from natural curved physiological paths followed when pushing or pulling an object.

Still referring still to FIG. 2, an exemplary computer and motor aided linear movement system 200 is provided. Generally, FIG. 2 illustrates examples of the structural elements 140 of the exercise system 100. In the illustrated system, the linear movement system 200 includes:

- a base 210, such as an aluminum extrusion or suitable material
- an upright support member 212 affixed to the base;
- a removable weightlifting bar 220 placeable into a guide element of the upright support member 212, or other geometry suitable for interfacing with the subject, such as a D-handle;
- a first end of a resistance cable 230 affixed to the weightlifting bar 220;
- a cable spool 242 affixed to a second end of the resistance cable 230;
- a resistance cable, such as flexible metallic cable, a fibrous cord, an about 0.053" sheathed Kevlar cord, or an about 3/32" T-100 cord; and/or
- an electric motor 240 configured to provide resistance to movement of the weightlifting bar 220 through the resistance cable 230.

As configured, the subject 110 stands on the floor, base 210, a foot support or cross-member 214 of the base 210, and/or an attachment thereto. The subject 110 pulls on the removable weightlifting bar 220 and/or on hand grips 222 affixed or attached to the weightlifting bar 220. Movement of the weightlifting bar 220 is continuous in motion, but is illustrated at a first point in time, $t_1$, and at a second point in time, $t_2$, for clarity. The subject pulls the weightlifting bar 220, such as along the z-axis. Movement of the weightlifting bar 220 is resisted by the electric motor 240. For example, the electric motor 240 provides a resistive force to rotation of the cable spool 242, which transfers the resistive force to the resistance cable 230 and to the weightlifting bar 220 pulled on by the subject 110. In one example, the electric motor 240 includes no gearbox, a fixed 5:1 gear, a variable gearbox, a low lash gearbox, and/or a MicroFlex drive to control motor torque. The torque produced by the motor is optionally made proportional to an analog voltage signal applied to one of the drive's analog inputs or is controlled by sending commands to set the torque value using a digital communications protocol.

Orientations

The linear movement system 200 is illustrated with the resistive cable 230 running in the z-axis. However, the resistive cable 230 optionally runs along the x-axis or any combination of the x-, y-, and z-axes. Similarly, the linear movement system 200 is illustrated for the user subject 110 standing on the floor. However, the exercise system 100 is optionally configured for use by the subject 110 in a sitting position or any user orientation. Further, the linear movement system 200 is illustrated with the subject 110 pulling up against a resistance. However, the subject is optionally pushing against a resistance, such as through use of a force direction changing pulley redirecting the resistance cable 230. Still further, the linear movement system 200 is illustrated for use by the subject's hands. However, the system is optionally configured for an interface to any part of the subject, such as a foot or a torso.

Resistance/Assistance Profiles

Traditional weight training pulls a force against gravity, which is constant, and requires the inertia of the mass to be overcome. Particularly, a force, F, is related to the mass, m, moved and the acceleration, g, of gravity, and the acceleration of the mass, a, through equation 1, $$F = mg + ma \qquad (eq.\ 1)$$

where the acceleration of gravity, g, is $$9.81 \frac{m}{\sec^2}.$$

Hence, the resistance to movement of the weight is non-linear as a function of time or as a function of movement of the user interactive element. In one example, the physical resistance supplied by the electric motor is maintained at an iso-inertial resistance through the solving of the equation F=ma, such that the force is maintained at an about constant level despite the acceleration and/or deceleration of the user interface, where about constant is less than 1, 5, 10, or 20 percent of a maximum load within a repetition.

Figure 3:
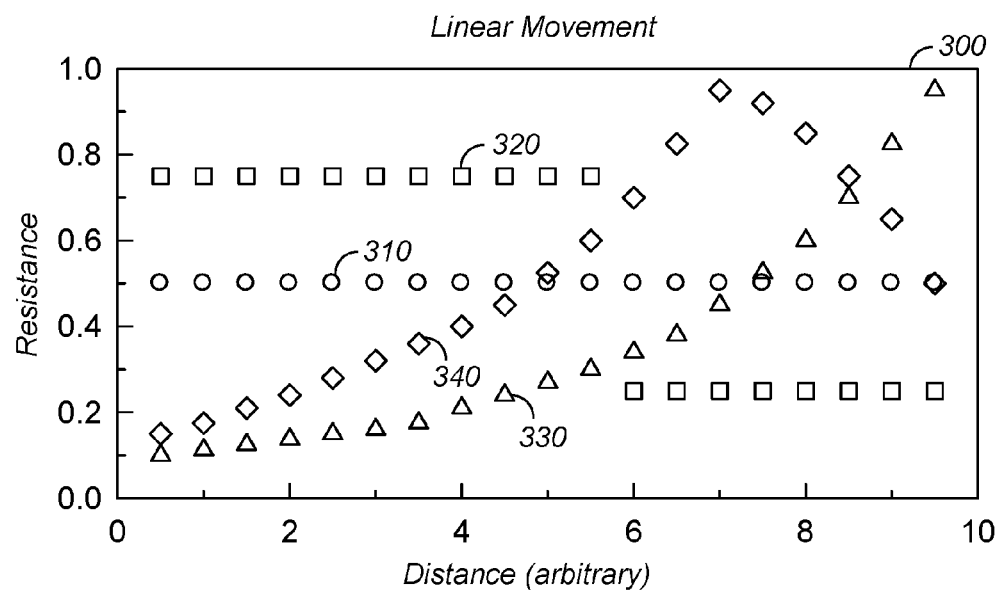
FIG. 3 provides exemplary resistance profiles for a linear movement.

Referring now to FIG. 3, linear movement resistance profiles 300 are illustrated, where both the resistance and distance are in arbitrary units. For traditional free weight strength training, the external resistance profile is flat 310 as a function of distance. For example, on a bench press a loaded weight of 315 pounds is the resistance at the bottom of the movement and at the top of the movement where acceleration is zero. At positions in between the external force required to accelerate the mass is dependent on the acceleration and deceleration of the bar. In stark contrast, the exercise system 100 described herein allows for changes in the resistance as a function of position within a single repetition of movement. Returning to the bench press example, it is well known that the biomechanics of the bench press result in an ascending strength curve, such that one may exert greater force at the end of the range of motion than at the beginning. Hence, when the lifter successfully lifts, pushes, or benches through the "sticking point" of the bench press movement, the person has greater strength at the same time the least amount of force needs to exerted as the mass is deceleration resulting in the musculature of the chest being sub-optimally loaded. Accordingly, a variable resistance profile starting with a lower resistance and then increasing to a peak resistance is more optimal for a bench press.

Still referring to FIG. 3, still an additional profile is a profile where the force at the beginning of the lift (in a given direction) is about equal to the force at the end of the lift, such as a weight of mass times gravity. At points or time periods between the beginning of the lift and the end of the lift (in a given direction) the force applied by the electric motor optionally depends on whether the bar is accelerating or decelerating. For example, additional force is applied by the motor during acceleration and no additional force is applied by the motor during deceleration versus a starting weight. For example, the applied force profile is higher than a starting weight or initial force as the load is accelerated and less than or equal to the initial load as it movement of the repetition decelerates.

Still referring to FIG. 3, more generally the resistance profile 300 is optionally set:

- according to predetermined average physiological human parameters;
- to facilitate therapy of a weak point in a range of motion;
- to accommodate restricted range of motion, such as with a handicap;
- to fit a particular individual's physiology;
- to fit a particular individual's preference;

in a pre-programmed fashion;
by parameters coded in a video game;
by parameters set by a trainer or medical professional;
in a modified and/or configurable manner; and/or
dynamically based on
    sensed values from the sensor 150; and/or
    through real-time operator 110 input.

Several optional resistance profiles are illustrated, including: a step-down function resistance profile 320, an increasing resistance profile 330, and a peak resistance profile 340. Physics based profiles include:
accurate solution of F=mg+ma;
accurate solution of $$F = mg + \begin{Bmatrix} ma, (a>0) \\ 0, (a \leq 0) \end{Bmatrix},$$

which prevents the resistance from dropping below the baseline, static resistance; and/or
accurate solution of F=mg+maximum, which maintains the maximum resistance developed when accelerating the load through the remainder of the lift.

Additional profiles include a step-up profile, a decreasing resistance profile, a minimum resistance profile, a flat profile, a complex profile, and/or any permutation and/or combination of all or parts of the listed profiles. Examples of complex profiles include a first profile of sequentially increasing, decreasing, and increasing resistance or a second profile of decreasing, increasing, and decreasing resistance.

In one example, the resistance force to movement of the subject interface varies by at least 1, 5, 10, 15, 20, 25, 50, or 100 percent within a repetition or between repetitions in a single set.

Reverse Movement

For the linear movement system 200, resistance profiles were provided for a given direction of movement, such as an upward push on bench press. Through appropriate mounts, pulleys, and the like, the resistance profile of the return movement, such as the downward movement of negative of the bench press, is also set to any profile. The increased load is optionally set as a percentage of the initial, static load. For example, the downward force profile of the bench press are optionally set to match the upward resistance profile, to increase weight, such as with a an increased weight "negative" bench press, or to have a profile of any permutation and/or combination of all or parts of the listed profiles.

Time/Range of Motion

One or more sensors are optionally used to control rate of movement of the resistive cable. For example, the electric motor 240 is optionally configured with an encoder that allows for determination of how far the cable has moved. The encoder optionally provides input to the controller 130 which controls further movement of the actuator and/or motor turn, thereby controlling in a time controlled manner movement or position of the resistive cable.

In one example, the exercise system 100 senses acceleration and/or deceleration of movement of the movable exercise equipment, such as the weightlifting bar 220. Acceleration and/or deceleration is measured using any of:
    an encoder associated with rotation of the electric motor;
    an accelerometer sensor configured to provide an acceleration signal;
    and/or
    a-priori knowledge of a range or motion of a given exercise type coupled with knowledge of:
        a start position of a repetition;
        a physical metric of the operator, such as arm length, leg length, chest size, and/or height.

Since putting an object into motion takes an effort beyond the force needed to continue the motion, such as through a raising period of a bench press, the forces applied by the motor are optionally used to increase or decrease the applied force based on position of movement of the repetition. The encoder, a-priori knowledge, physical metrics, and/or direct measurement with a load cell, force transducer, or strain gauge are optionally used in formulation of the appropriate resistance force applied by the electric motor 240 as a function of time.

Exercise Types

Thus far, concentric and eccentric exercises configurable with the exercise system 100 have been described. Optionally, isometric exercises are configurable with the exercise system 100. An isometric exercise is a type of strength training where a joint angle and a muscle length do not vary during contraction. Hence, isometric exercises are performed in static positions, rather than being dynamic through a range of motion. Resistance by the electric motor 240 transferred through the resistive cable 230 to the weightlifting bar 220 allows for isometric exercise, such as with a lock on the motor or cable, and/or through use of a sensor, such as the encoder. An additional example is an interface for grip strength operating against the motor.

Rotational Movement

Thus far, the linear movement system 200 species of the exercise system 100 has been described. Generally, elements of the linear movement system 200 apply to a rotational movement system 400 species of the exercise system 100 genus. In a rotary movement system, the electric motor 240 provides resistance to rotational force.

Figure 4:
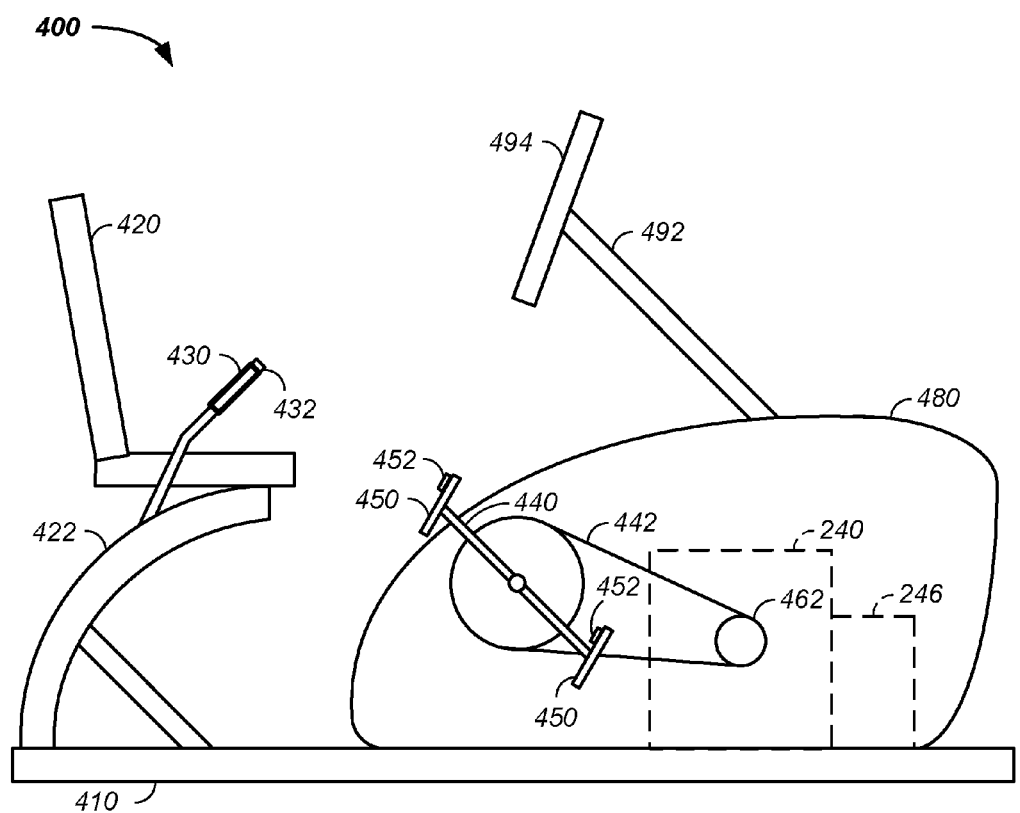
FIG. 4 illustrates a rotary exercise system configured with electric motor resistance.

Referring now to FIG. 4, a non-limiting example of a rotational movement system 400 is illustrated, which is a species of the exercise system 100. The rotational movement system 400 is illustrative in nature and is used for facilitating disclosure of the system. Further, the species of the rotational movement system 400 is to a specific form of the exercise system 100, for clarity of presentation. However, the illustrated rotational movement system 400 is only one of many possible forms of the exercise system 100 and is not limiting in scope.

Still referring still to FIG. 4, an exemplary computer and motor aided rotational movement system 400 is provided. Generally, FIG. 4 illustrates examples of the structural elements 140 of the exercise system 100. In the illustrated system, the rotational movement system 400 includes:
    a support base 410;
    an upright support member 422 affixed to the base;
    an operator support 420, such as a seat, affixed to the upright support member 422;
    a hand support 430 affixed to the upright support member 422;
    a crank assembly 440 supported directly and/or indirectly by the support base 410 or a support member;
    pedals 450 attached to the crank assembly 440;
    an electric motor 240;
    a rotational cable 442 affixed to the crank assembly 440 and to the motor 240;
    control electronics 246 electrically connected to at least one of the electric motor 240 and controller 130;
    a display screen 494 attached to a display support 492, which is directly and or indirectly attached to the support base 410; and/or an aesthetic housing 480, which is optionally attached, hinged, or detachable from the support base 410.

In stark contrast with a power generation system where a user pedals a crank and generates power, the system herein described optionally uses an electric motor to provide a resistance against which the person exercising needs to exert force.

Orientations

As with the with linear movement system 200, the orientations of the rotational movement system 400 are optionally configurable in any orientation and/or with alternative body parts, such as with the hands and arms instead of with feet and legs.

Resistance/Assistance Profiles

Figure 5:
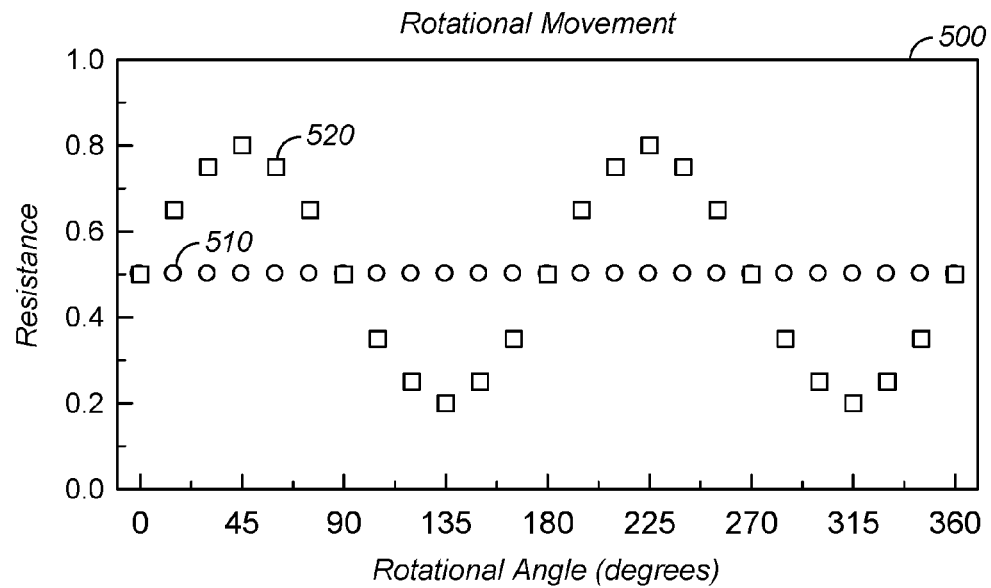
FIG. 5 provides exemplary resistance profiles for a rotary movement.

As described, supra, with respect to the linear movement system 200, traditional rotary systems have a preset resistance, which is either flat or based upon a fixed cam or set of fixed cams. Referring now to FIG. 5, rotational movement resistance profiles 500 are illustrated, where the resistance is in arbitrary units as a function of rotation angle theta. For traditional rotation systems, the resistance profile is flat 510 as a function of rotation. In stark contrast, the exercise system 100 described herein allows for changes in the resistance as a function of rotation within a single revolution of movement and/or with successive revolutions of the rotating element. Typically, resistance variation is a result of changes in the electric motor supplied resistance.

An example of rotation of a bicycle crank illustrates differences between traditional systems and resistance profiles available using the rotational movement system 500. A flat resistance profile versus rotation 510 is typical. However, the physiology of the body allows for maximum exerted forces with the right leg at about 45 degrees of rotation of the crank (zero degrees being the 12 o'clock position with a vertical rotor) and maximum exerted forces by the left leg at about 225 degrees of rotation of the crank. The computer controlled electric motor 240 allows variation of the resistance profile as a function of rotational angle 520. Unlike a cam system or a bicycle equipped with an elliptical crank, the resistance profile is alterable between successive revolutions of the crank via software and/or without a mechanical change.

Still referring to FIG. 5, more generally the resistance profile 500 of the rotational exercise system 400 is optionally set:
- according to predetermined average physiological human parameters;
- to facilitate therapy of a weak point in a range of motion;
- to accommodate restricted range of motion, such as with a handicap;
- to fit a particular individual's physiology;
- to fit a particular individual's preference;
- in a pre-programmed fashion;
- according to a video game program;
- according to an exercise program on a display screen;
- in a modified and/or configurable manner; and/or
- dynamically based on
  - sensed values from the sensor 150; and/or
  - through real-time operator 110 input.

Several optional rotational resistance profiles are possible, including: a step function resistance profile, a changing resistance profile within a rotation and/or between rotations, a range or programs of resistance profiles. Additional profiles include any permutation and/or combination of all or parts of the profiles listed herein for the linear movement system 200 and/or the rotational movement system 400.

Combinatorial Linear and Rotation Systems

Figure 6:
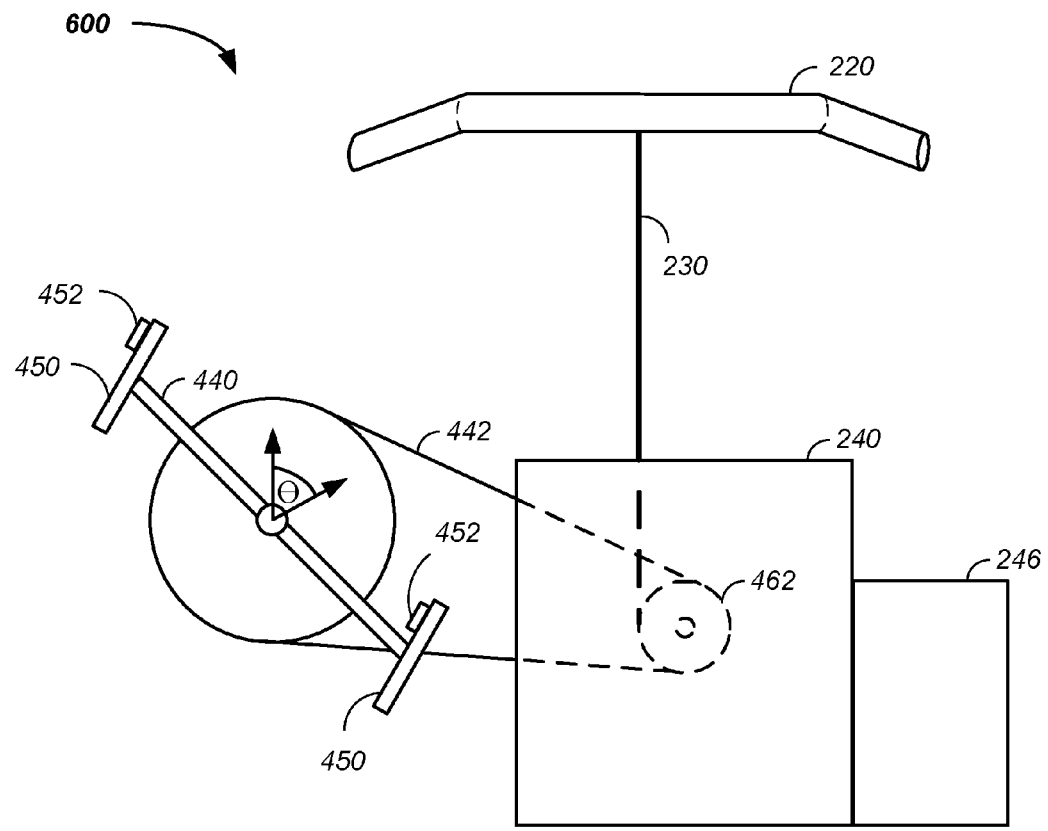
FIG. 6 illustrates a combined linear and rotary exercise system.

Referring now to FIG. 6, a combinatorial movement system 200 is illustrated. In the illustrated example, a single electric motor 240 is used for control of two or more pieces of exercise equipment, such as:
- an isometric station;
- a linear movement system 200; and
- a rotational movement system 400.

Generally, the single electric motor 240 optionally provides resistance to 1, 2, 3, 4, 5, or more workout stations of any type.

Still referring to FIG. 6, an exercise system is figuratively illustrated showing interfaces for each of: (1) a linear movement system 200 and (2) a rotational movement system 200 with a motor 240 and/or motor controlled wheel 462. The combinatorial movement system 600 is illustrative in nature and is used for facilitating disclosure of the system. However, the illustrated combinatorial movement system 600 is only one of many possible forms of the exercise system 100 and is not limiting in scope.

Sensors

Optionally, various sensors 150 are integrated into and/or are used in conjunction with the exercise system 100.

Operator Input

A first type of sensor includes input sources to the computer from the operator 110. For example, the hand support 430 of the rotational movement system 400 is optionally configured with one or more hand control 432 buttons, switches, or control elements allowing the operator 110 to adjust resistance and/or speed of the electric motor 240 within a repetition and/or between repetitions. For example, an increase weight button is optionally repeatedly depressed during raising of a weight, which incrementally increases the load applied by the electric motor 240. A similar button is optionally used to decrease the weight. Similarly foot control buttons 452 are optionally used to achieve the same tasks, such as when the hands are tightly gripped on a weightlifting bar.

Instrumentation Sensor

A second type of sensor 150 delivers information to the computer of the exercise system 100. In a first example, the pedals 450 of the bicycle assembly are optionally equipped with sensors 150 as a means for measuring the force applied by a operator 110 to the pedals. As a second example, the linear motion system 200 and/or rotational motion system 400 optionally contains sensors 150 for measuring load, position, velocity, and/or acceleration of any movable element, such as the pedals 450 or the weightlifting bar 200.

For example, muscle loading is controlled using the resistance force exerted on the bar by the electric motor. Position, velocity, and acceleration data are provided by an encoder on the motor and are used as feedback in the control system. For additional muscular overload, often more weight is lowered than can be raised. The lowering or eccentric phase of the exercise can be controlled in real-time for eccentric overload. Muscle loading control and data acquisition is optionally performed, for example, in a dataflow programming language where execution is determined by the structure of a graphical block diagram which the programmer connects different function-nodes by drawing wires, such as LabView® or other suitable software.

Radio-Frequency Identification

A third type of sensor 150 delivers information to the computer of the exercise system 100 from the operator. For example, the operator wears a radio-frequency identification (RFID) tag, such as in a belt, shoe, wallet, cell phone, article of clothing, or an embedded device. The radio frequency identification identifies the operator to the exercise system 100 along with information, such as any of:

an operator name;
an operator gender;
an operator age;
an operator height;
an operator weight;
an operator physical characteristic, such as arm length, leg length, chest size for an exercise like a bench press;
an operator workout preference;
an operator workout history, such as recorded onto recording media or sent to the cloud; and
an operator goal.

The radio-frequency identification tag is of any type, such as active or battery powered, passive, and battery assisted passive. Generally, wireless signal is received by the exercise equipment 100 from a broadcast source, such as from a global positioning system or radio-frequency identification (RFID) tag.

Computer

The motor drive controller 130 is optionally connected to a microprocessor or computer and power electronics that are used to control the electric motor 240. The power electronics are connected to a power supply such as a battery or power outlet. The computer, the electric drive unit, and the sensors 150 optionally communicate with one another to form feedback control loops allowing the profile of the force and/or resistance applied to the operator 110. The computer optionally provides: a user interface, data storage and processing, and/or communication with other computers and/or a network.

A visual feedback system or display screen 494 is also optionally used to provide the user with immediate feedback on velocity tracking ability and/or other exercise related parameters. Velocity tracking is particularly useful for systems designed for patients in rehabilitation settings.

Gaming System

In yet another embodiment, the exercise system 100 is used in conjunction with a gaming system 700, such as a video game system where the exercise system provides real physical resistance to an interface, the results of which are integrated into a video game, such as running on a game console.

Figure 7:
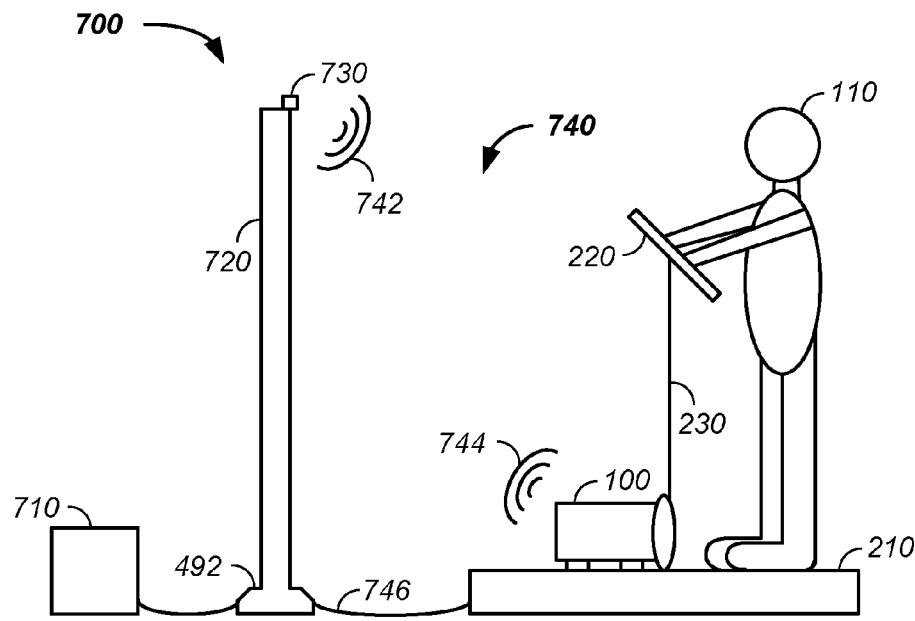
FIG. 7 provides an exercise system linked to a game system.

Referring now to FIG. 7, an example of the exercise system 100 used in combination with a gaming system 700 is illustrated. This example is used for clarity of presentation and is not limiting in scope. In this example, the user 110 uses the exercise system 100, which is in communication with the gaming system 700. The gaming system 700 optionally includes:

a game console 710;
a display device 720, such as a display screen 494;
a communication element 730;
a sensing element 740; and/or
a user controller.

Game Console

A game console 710 is an interactive entertainment computer or customized computer system that produces a video display signal that is optionally used with a display device, described infra. Herein, a game console includes a video game system and/or a computer system. The game console 710 is optionally embedded with and/or in the exercise system 100. Examples of game consoles 710 include: a computer in the exercise system 100 or any form of proprietary or commercially available gaming system, such as those produced by Nintendo® (Kobe, Japan), Sony® (Tokyo, Japan), Microsoft® (Redmond, Wash.), or the like. Particular examples of video game consoles include the Wii® (Nintendo, Kobe, Japan), PlayStation® (Sony, Tokyo, Japan), Xbox®, (Microsoft, Redmond, Wash.), or the like.

Display Device

A display device 720 outputs a video display signal, such as from an external game console 710 or from an internal computer of the exercise system 100. Examples of a display device 720 include: a television, a monitor, an optically emitting diode, an organic light emitting diode, or a personal display device, such as a smart phone or tablet. The display device 720 is optionally used to display output of: a video game, an exercise program, a physical therapy routine, and/or a medical program. The display device 720 optionally displays images or video encouraging the user 110 of the exercise system 100 to achieve a goal, such as a competitors 828 or virtual competitors performance, explicit technical information on performance, or video game like animation of the user's 110 progress on a given lift or use of the exercise system 100. For example, the display device 720 is optionally used to display a set point resistance and display an updated visual indicator comparing user 110 performance with the set point. Additional optionally displayed technical information includes any of: number of repetitions, force generated, power generated, velocity, and acceleration.

Communication Element

A communication element 740 includes any element used to convey any form of information from the exercise system 100 to the gaming system 700 or vise-versa. Examples of a communication element 740 include a wired and/or wireless digital link 726 between the exercise system 100 and game system 700 carrying analog and/or digital information; a signal transmitted from the gaming system wirelessly 742 using any part of the electromagnetic spectrum; an optical signal; and a signal transmitted from the exercise system wirelessly 744 using any part of the electromagnetic spectrum. For example, any signal generated via the interaction of the user 110 with the exercise system 100 is optionally transmitted to the gaming system 700. Examples of transmitted signals include output of any of: a sensor; an accelerometer; a user input; or a spatial location system, such as via the use of a controller described infra. Similarly, examples of transmitted signals include any output from the gaming system 700 received by the exercise system 100. Still further, examples of "transmitted" signals include any information received from the user, such as position, and/or received by the gaming system, such as through a sensing element 730 described infra.

Sensing Element

The sensing element 730 includes any system, sensor, and/or element used to receive and/or derive information about the environment and/or the user 110. For example, the sensing element 730 receives 3-D information from a controller, motion information from an accelerometer, physiology information from a user sensor, and/or environment information, such as through infrared detection, use of any portion of the electromagnetic spectrum, and/or via a temperature, pressure, work, or force sensor. Examples of sensing elements 730 include induced signals, such as reflectance of an ultraviolet, visible, and/or infrared source; a one, two, or three dimensional accelerometer; a light sensor or light gun sensor; a yaw, tilt, or roll sensor; a rotation sensor; a sensor bar; a sensor array; and/or combinatorial use of multiple sensor types. Preferably, the sensing element 730 is configured with an analyzer to interpret the received signals and a link to the gaming system 700 or game console 710.

User Controller

The user controller senses actions of the user 110. The user controller uses input from the user 110 and/or from the controller 130. The user controller directly and/or indirectly sends collected data and/or information to the gaming system 700. In one case, the user controller responds to a verbal command from the user, such as a command to increase or decrease the resistance supplied by the electric motor; a command to increase or decrease the rate of the repetition; and/or a stop/help/quit/end command.

Games

Generally, a video game is any electronic game that involves human interaction with a user interface to generate visual feedback on a video device. Hence, any list of video games is necessarily non-inclusive. However, some video games lend themselves to interaction and use of the exercise system 100, such as games involving:
- a pumping action, such as filling an animated liquid or gas container;
- a lifting action, such as a bench press, overhead press, or squat; and/or
- a pedaling action.

Additional video game examples include use of the exercise system in a strongman competition video game or in a fishing game pulling against a running or fighting fish. Generally, any movement of an element of the exercise system 100 is optionally visualized and/or integrated into the game system 700.

Online/Internet/Cloud

Figure 8:
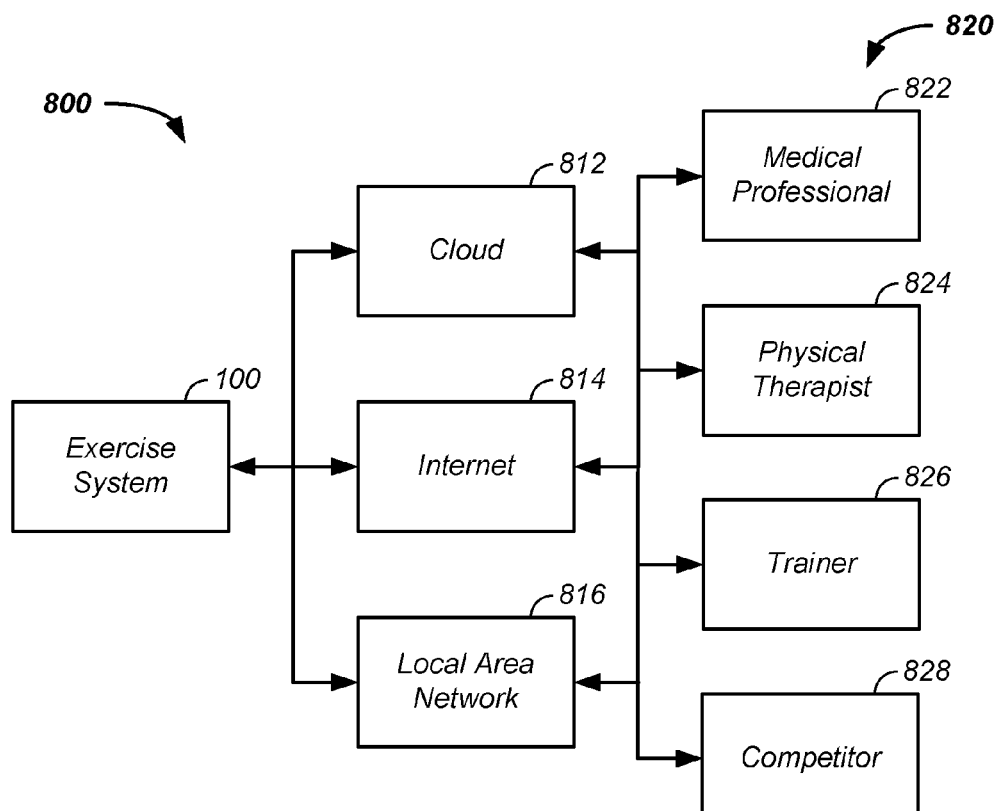
FIG. 8 illustrates data communication with a secondary user.

Referring now to FIG. 8, any of the exercise system 100 inputs and/or outputs are optionally shared using a computer information delivery system 800 with a secondary user 820.

Still referring to FIG. 8, in one example the exercise system 100 shares information using the cloud 812, the internet 814, or over a local area network 816 with the secondary user 820. Herein, the cloud 812 is a general term for anything that involves delivering hosted services over the Internet; the internet 814 is a vast computer network linking smaller computer networks, commercial systems, educational systems, government systems, and/or individual computers worldwide using the same set of communications protocols; and the local area network 816 refers to any intranet, personal computer, and/or workstation.

Still referring to FIG. 8, in another example the exercise system 100 shares information using the computer information delivery system 800 with the secondary user 820, where the secondary user optionally includes: a medical professional 822, a physical therapist 824, a trainer 826, and/or a competitor 828.

Remote Access

Remote accessibility of data from the exercise system 100 allows for the secondary user 820 to conveniently and effectively monitor and/or manage a health and/or fitness routine of the user 110 of the exercise system 100.

Still referring to FIG. 8, since the exercise system 100 preferably uses computer control and/or a processor in control of the electric motor 240, the computer is available and is optionally:
- connected with a second processor of the exercise system;
- used to process raw exercise system 100 generated data to yield information;
- connected with information delivery and/or sharing hardware;
- used to deliver/share the raw data and/or processed information;
- equipped for remote monitoring and/or remote connectivity, such as with the secondary user 820; and/or
- configured to record/share data exercise data as the subject or user 110 uses the exercise system 100.

The recorded exercise data optionally includes output of any sensor or executed program parameter of the exercise system 100, such as set load, actual load, load velocity, acceleration of the load, resulting power, range of motion, and/or number of repetitions and/or sets. The recorded exercise data is optionally available to any of the secondary users 820, such as the physical therapist 824 or trainer 826, such as via the cloud 812, internet 814, and/or local area network 816. The secondary user 820 optionally uses the recorded exercise data for verification of the user 110 performing a set exercise program as prescribed by the medical professional 822 or set by the physical therapist 824 or trainer 826 and/or to determine where the user 110 fails to achieve specific desired goals. The data availability allows the secondary user 820 to monitor progress and optionally to adjust exercise parameter goals remotely. The remote accessibility allows for effective health management, professional health monitoring, reduces secondary user time requirements, allows an in-home fitness system for frequent access by the user, and allows for accessibility by home bound individuals. Still further, the therapist 824 or trainer 826 optionally has remote access to the exercise system 100 and is allowed to update the exercises that the user 110 is to perform and to adjust weights, resistance, loads, and/or number of repetitions or sets to be performed. As described, supra, resistance within a repetition is optionally configured with any linear or rotational movement resistance profile 300, 500.

Competitor

Any of the data and/or information generated by the user 110 using the exercise system 100 is optionally shared with a competitor 828, such as another user of an equivalent exercise system located anywhere in the world. The competition is optionally serial, overlapping in time, or in real time. The competitor is optionally any number of competitors using any number of exercise machines. The competition is optionally in the form of a weightlifting/power/strongman competition and/or is part of a video game. Teams are optionally formed and ranks of individuals and/or teams are optionally shared as a function of age, gender, location, and/or class. The competitor 828 is optionally a virtual computer generated competitor. Presence on the display device 720 of a competitor is optionally an image, a virtual character, or a real picture/video of the competitor.

Virtual Trainer

Optionally, the computer of the exercise system 100 is configured with hardware and/or software means for providing a virtual trainer. The virtual trainer is optionally configured with software coded algorithms for adjusting any parameter of the exercise system 100 toward a user 110, secondary user 820, or exercise system programmer goal. The virtual trainer is optionally configured with:
- prerecorded or interactive voice and/or video, such as a training tip;
  - voice recognition and context interpretation software for interpretation and/or implementation of a routine set to a user 110 specified goal;
  - an exercise performance analyzer, which translates and interprets raw output of the exercise system 100 into summary information, such as a graph or a graph/time-series analysis of an exercise parameter; and/or
  - a pep talk.

Optionally, any chat, video, and/or analysis element of the virtual trainer is available to the secondary user 820. Still further, the exercise system 100 is optionally configured with an intelligent software assistant and knowledge navigator functioning as a personal assistant application. The software assistance optionally uses a natural language user interface to answer questions, make recommendations, and perform actions by delegating requests, such as to a secondary user or a secondary external and remote computer system. Optionally, the exercise system 100 virtual trainer is configured to adapt to the user 110, such as to individual training preferences over time and/or humor and to personalize the training routine or virtual trainer interfacing options.

In still yet another embodiment, any of the accessibility options and/or parameters are optionally accessed, by the secondary user or virtual trainer, in real-time during exercise by the user 110 and/or at a time period after the exercise by the user 110 has been completed.

In yet still another embodiment, any of the computer information delivery system 800 elements or remote access elements, described supra, are optionally implement with any of the gaming system 700 elements and vise-versa.

In yet another embodiment, the exercise system is optionally configured to set a control force or resistance according to a formula, such as F=mg+ma, or to use another control variable. For example, the exercise system 100 is optionally set to control the power profile, which is set by multiplying the measured force times the measured velocity. Setting the power as the resistance is distinct from use of gravity as a weight and allows for a new form of resistance training. For instance, a method of use of the exercise system includes one or more of:

setting a goal resistance or force;
measuring the force and velocity;
calculating an output power;
comparing the output power with a power set point, which is optionally time-varying;
computing a force and velocity needed to reach the desired power set point; and
updating the goal resistance or setting a power goal;
measuring the force and velocity;
calculating an output power;
comparing the output power with the power goal;
computing a force and velocity needed to reach the desired power set point; and
updating the goal resistance based on the user performance to meet the power goal.

Any of the elements described, supra, such as the visual representation of the goal or achievement, use of a virtual trainer, and/or sharing information with the secondary user 820 are optionally incorporated with this embodiment.

Microgravity

In yet another embodiment, the exercise system 100 described herein is designed for use in a microgravity environment. Variations include use of lightweight materials, straps for holding an astronaut relative to the exercise system, and an emphasis on foldable and/or collapsible parts. In one case, equally applicable to full gravity environments, energy generated through use of the exercise system is captured and stored in a battery.

Compact/Reconfigurable System

As described in U.S. patent application Ser. No. 12/545,324, which is incorporated herein, the system 100 is optionally configured as a compact strength training system that provides the benefits associated with free weight lifting and/or aerobic training. Optionally, structure of the exercise system 100 is optionally manually or robotically reconfigurable into different positions, such as a folded position for storage. For example, the weightlifting bar 220 folds, the operator support 420 folds, and/or the support base 410 folds or telescopes.

Still yet another embodiment includes any combination and/or permutation of any of the elements described herein.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A method for a primary user exercising in communication with a remote secondary user, comprising the steps of:
    the primary user using an exercise system, said exercise system comprising:
        a primary user interface configured for interaction with the primary user;
        an electric motor, said electric motor configured to provide a resistive force to said primary user interface;
        a controller communicatively coupled with said electric motor, said controller configured to control the resistive force supplied by said electric motor as a function of time; and
        means for communication with the secondary user, said means for communication communicatively coupled with said controller; and
    communicating output of said exercise system with the remote secondary user,
    wherein said controller dynamically maintains the resistive force supplied by said electric motor within twenty percent of an iso-inertial force as a function of time within one-half of a repetition by adjusting the resistive force as a function of monitored acceleration of said primary user interface.

2. The method of claim 1, further comprising the step of: transferring via a flexible material the resistive force supplied by the electric motor to the primary user interface.

3. The method of claim 1, wherein the secondary user comprises at least one of:
    a physical therapist;
    a coach;
    a game or contest opponent; and
    a trainer.

4. The method of claim 1, further comprising the step of: the secondary user remotely configuring the controller with a program.

5. The method of claim 4, further comprising the step of: the exercise system communicating historical use of the exercise system by the primary user to an algorithm of the remote secondary user.

6. The method of claim 1, further comprising the step of: using a sensor to measure at least one of:
    force applied by the primary user to the primary user interface;
    a physiological measure of the primary user;
    acceleration of the primary user interface; and
    motion of the primary user interface.

7. The method of claim 6, further comprising the step of: using output of said sensor, said controller dynamically adjusting the resistive force supplied by said electric motor within a repetition of movement of the primary user interface.

8. The method of claim 6, further comprising the step of: using said electric motor to increase the resistive force when said sensor outputs data indicating positive acceleration of said primary user interface.

9. The method of claim 6, further comprising the step of: decreasing the resistive force supplied by said electric motor when output of said sensor indicates sticking point reduced motion of said primary user interface.

10. The method of claim 1, further comprising the step of: said controller dynamically adjusting, by at least twenty percent, the resistive force supplied by said electric motor during a repetition of movement of the primary user interface by the primary user.

11. The method of claim 1, wherein said means for communication comprise at least one of:
    use of an internet;
    a wireless digital link;
    use of a cloud; and
    use of a local area network.

12. The method of claim 1, further comprising the step of: storing energy generated by use of said exercise system into a battery.

13. The method of claim 1, further comprising the steps of:
    using said controller and output of a heart rate monitor to vary the resistive force supplied by said electric motor to maintain a heart rate of the primary user in a target range.

14. The method of claim 1, further comprising the step of: said exercise system responding to a verbal control command.

15. The method of claim 1, further comprising the step of: said controller computing the resistive force using at least one of:
    an equation of $F=mg+ma$;
    an equation of $F=mg$;
    an equation relating F to ma; and
    an equation adjusting F with maximum, wherein maximum comprises a measure of maximum achieved resistance in said repetition,
    wherein F comprises the resistive force, m comprises a simulated mass, a comprises a measure of acceleration, and g comprises a constant.

16. The method of claim 3, wherein said trainer comprises a virtual trainer.

17. The method of claim 16, said virtual trainer configured to provide at least one of:
    a training tip;
    a pep talk; and
    a personalized training routine.

18. The method of claim 1, said secondary user comprising a secondary external and remote computer system.

19. The method of claim 1, said controller further comprising:
    an intelligent software assistant and knowledge navigator functioning as a personal assistant application.

20. The method of claim 1, further comprising the step of: said controller dynamically selecting an equation used to determine the resistive force.

* * * * *